United States Patent
Bor

(10) Patent No.: US 12,150,709 B2
(45) Date of Patent: Nov. 26, 2024

(54) VISUAL AXIS IDENTIFICATION SYSTEMS AND METHODS

(71) Applicant: Alcon Inc., Fribourg (CH)

(72) Inventor: Zsolt Bor, San Clemente, CA (US)

(73) Assignee: Alcon Inc., Fribourg (CH)

( * ) Notice: Subject to any disclaimer, the term of this patent is extended or adjusted under 35 U.S.C. 154(b) by 737 days.

(21) Appl. No.: 17/225,252

(22) Filed: Apr. 8, 2021

(65) Prior Publication Data
US 2021/0369105 A1 Dec. 2, 2021

Related U.S. Application Data

(60) Provisional application No. 63/033,327, filed on Jun. 2, 2020.

(51) Int. Cl.
| | |
|---|---|
| A61B 3/00 | (2006.01) |
| A61B 3/113 | (2006.01) |
| A61B 3/14 | (2006.01) |
| A61B 3/103 | (2006.01) |

(52) U.S. Cl.
CPC ............ *A61B 3/0091* (2013.01); *A61B 3/113* (2013.01); *A61B 3/14* (2013.01); *A61B 3/0025* (2013.01); *A61B 3/103* (2013.01)

(58) Field of Classification Search
CPC ........ A61B 3/113; A61B 3/152; A61B 3/0091
USPC ....................................................... 351/208
See application file for complete search history.

(56) References Cited

U.S. PATENT DOCUMENTS

| | | | | |
|---|---|---|---|---|
| 4,923,297 A * | 5/1990 | Arndt | ...................... | A61B 3/12 351/208 |
| 5,474,548 A * | 12/1995 | Knopp | .................... | A61F 9/008 606/4 |
| 5,532,771 A * | 7/1996 | Johnson | ................... | A61B 3/14 359/205.1 |
| 7,160,288 B2 * | 1/2007 | Sumiya | ............... | A61F 9/00804 606/4 |
| 9,895,100 B2 * | 2/2018 | Port | ..................... | A61B 5/7282 |
| 10,548,770 B2 * | 2/2020 | Rathjen | .................. | A61F 9/008 |
| 10,786,150 B2 * | 9/2020 | Durr | .................... | A61B 3/0025 |
| 2003/0163122 A1 * | 8/2003 | Sumiya | ............... | A61F 9/00804 351/200 |
| 2005/0046794 A1 | 3/2005 | Silvestrini et al. | | |
| 2008/0077121 A1 * | 3/2008 | Rathjen | .............. | A61F 9/00827 606/5 |

(Continued)

FOREIGN PATENT DOCUMENTS

WO 2014172621 A2 10/2014

*Primary Examiner* — Zachary W Wilkes

(57) ABSTRACT

The devices and methods described herein provide improved methods for accurately identifying and locating the visual axis of the eye and its intersection with the iris plane. In one embodiment, a visual axis identification system includes a fixation light source, a camera, and a processing system. During operation thereof, the patient focuses their gaze onto two or more fixation light spots provided by the fixation light source upon an optical axis thereof, which creates two or more corresponding images on or near to the patient's retina. The patient's head is then rotated relative while the patient continuously maintains their gaze on the fixation light spots. The patient's visual axis may be located by determining the location of the optical axis of the fixation light source relative to the patient's eye when the centers of the multiple images coincide in the patient's view.

11 Claims, 18 Drawing Sheets

(56) References Cited

U.S. PATENT DOCUMENTS

| | | | | |
|---|---|---|---|---|
| 2012/0133889 A1* | 5/2012 | Bergt | .................. | A61B 3/113 |
| | | | | 351/209 |
| 2016/0128562 A1* | 5/2016 | Durr | .................. | A61B 3/0091 |
| | | | | 351/205 |
| 2016/0213301 A1* | 7/2016 | Port | .................. | A61B 5/743 |
| 2022/0148218 A1* | 5/2022 | Weitz | .................. | A61B 3/113 |
| 2022/0287562 A1* | 9/2022 | Yoon | .................. | A61B 3/1173 |

* cited by examiner

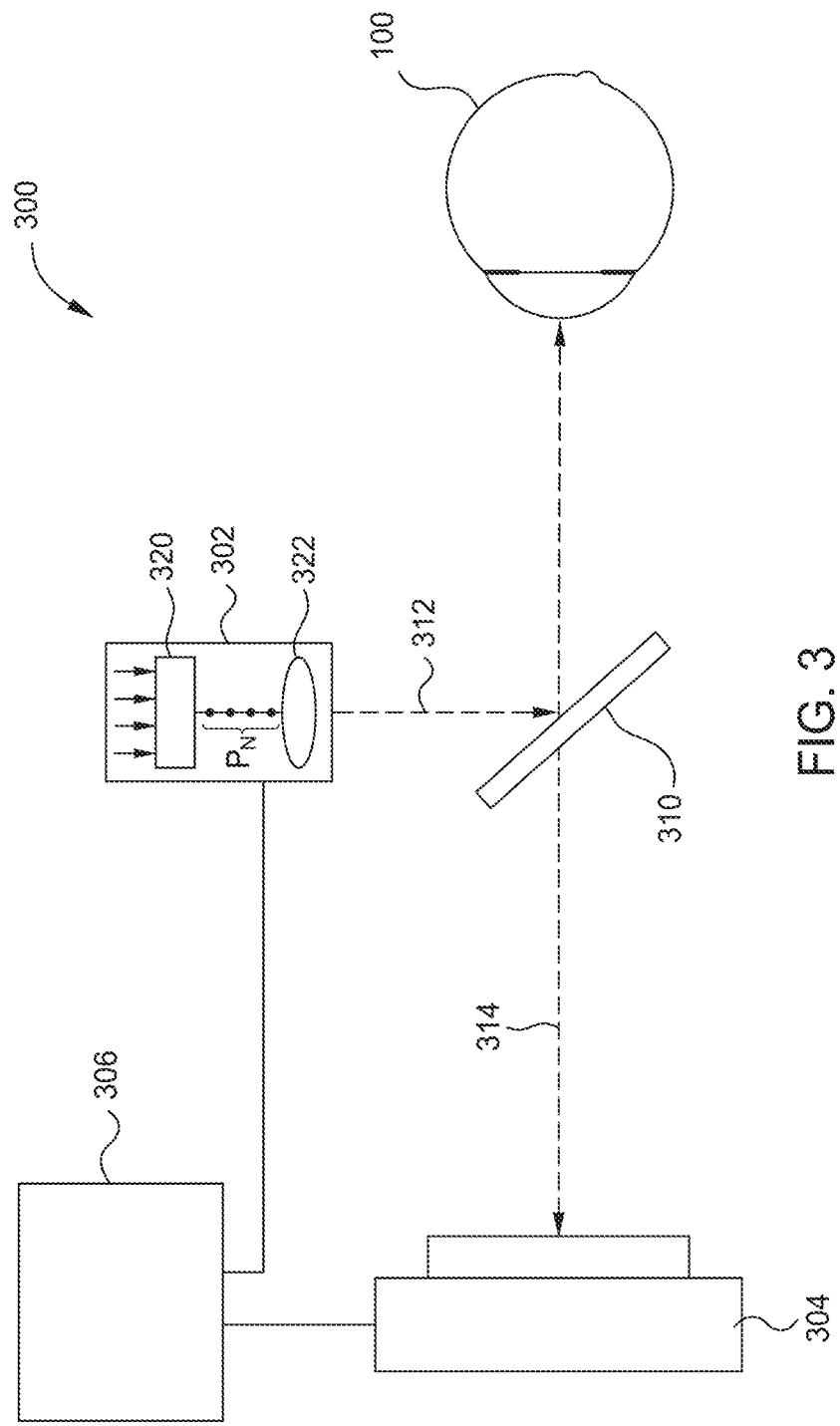

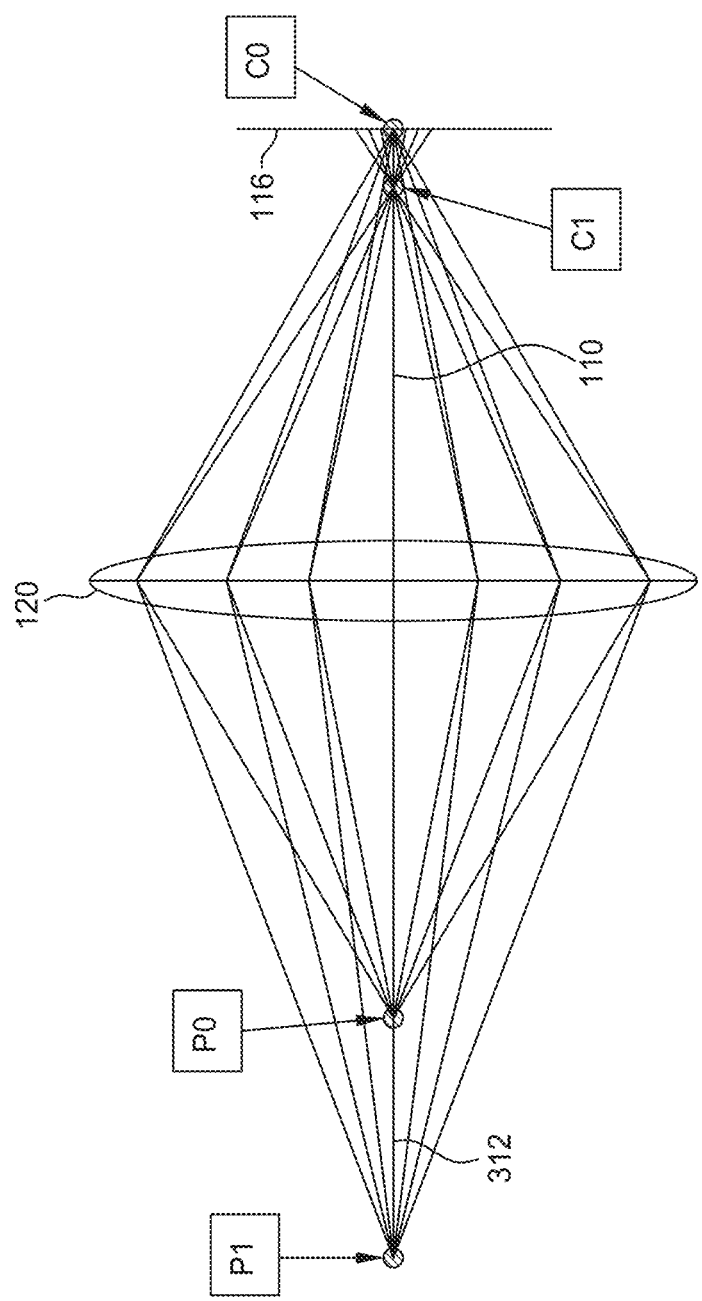
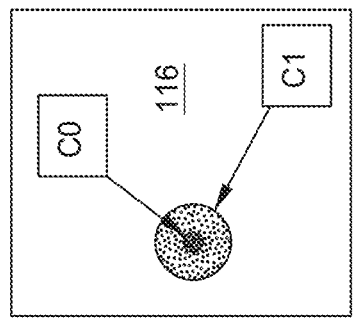
FIG. 4A
FIG. 4B

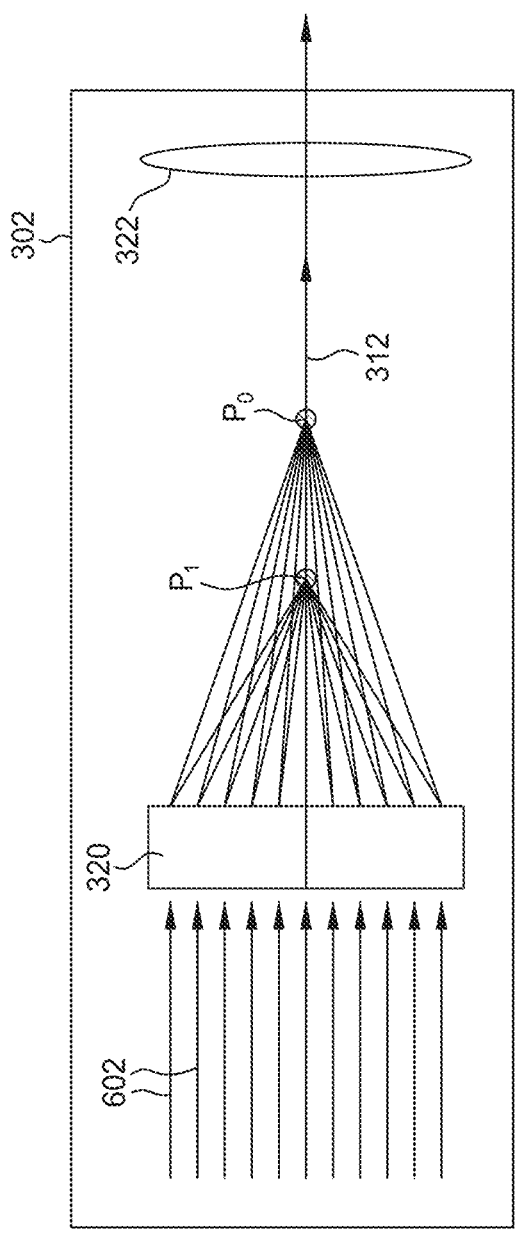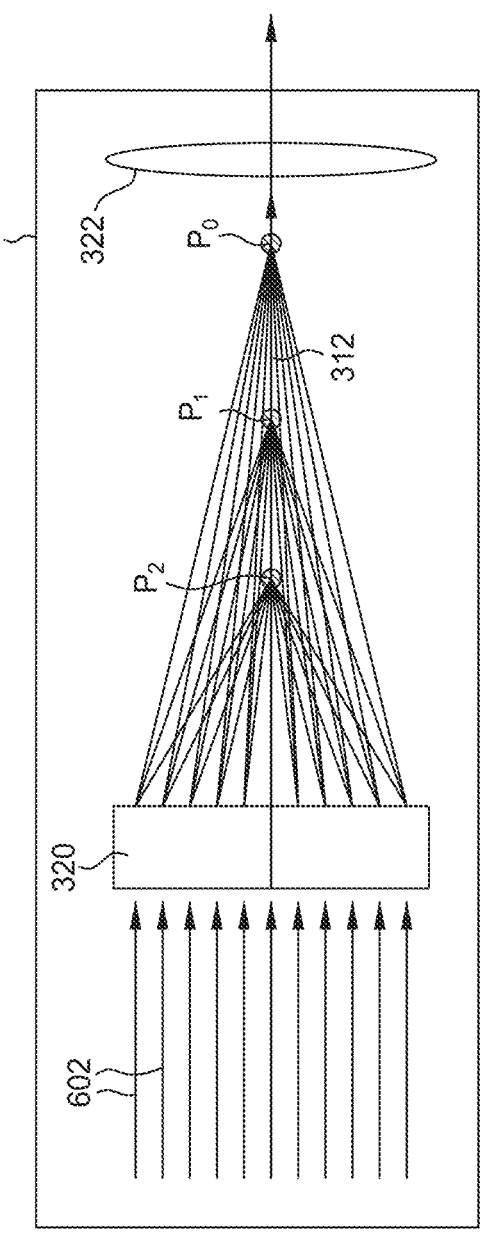

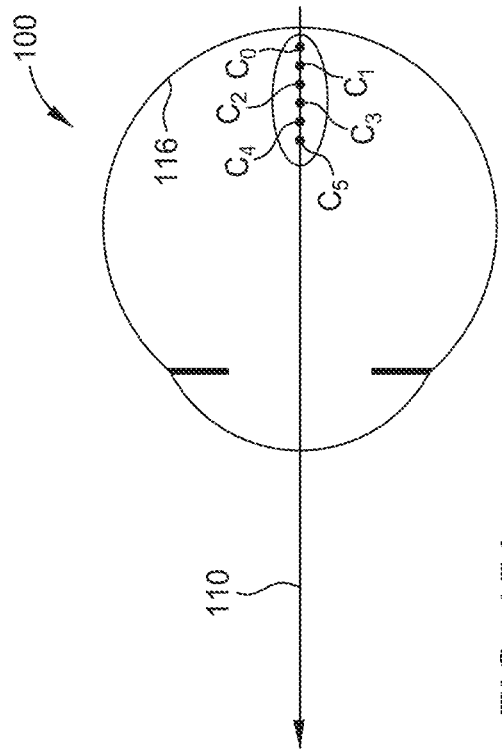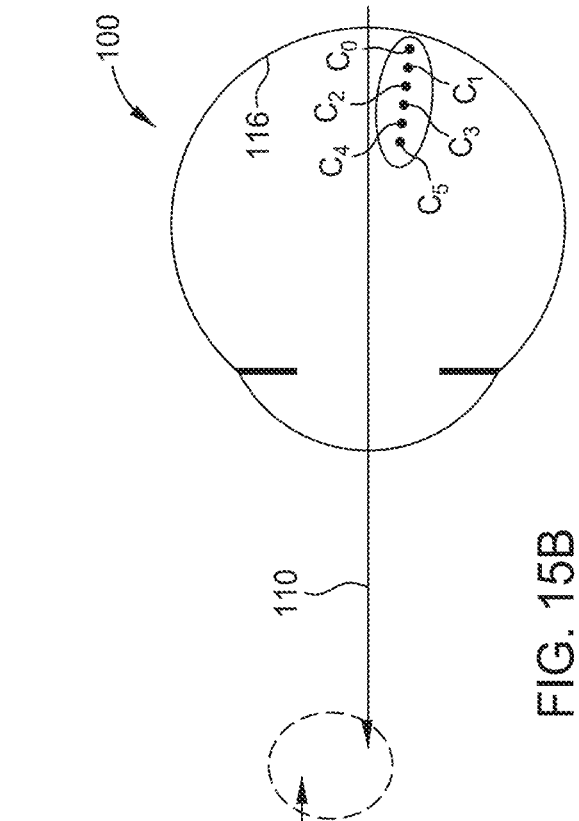
FIG. 15A
FIG. 15B

VISUAL AXIS IDENTIFICATION SYSTEMS AND METHODS

BACKGROUND

Field

Embodiments of the present disclosure generally relate to ophthalmic methods and apparatus for characterization of optical properties of the eye, and more particularly, to methods and apparatus for accurate identification of the visual axis of the eye.

Description of the Related Art

Conventional techniques for presbyopic treatments typically include determining the relative location of the visual axis of the patient's eye. Accurate determination of this axis is essential for effective placement of bifocal, multifocal, and extended depth of focus (EDOF) intraocular lenses (IOLs). Even a slight misalignment of these lenses may significantly impede any benefits intended by surgical implantation thereof. Other examples of presbyopic treatments that may also benefit from the determination of the visual axis include LASIK, PresbyLASIK or multifocal LASIK, and photorefractive keratectomy (PRK) surgery, to name a few.

The visual axis is one's actual line of sight, which is a straight line joining the fovea of the eye, a small depression in the retina and the clearest point of vision, with a fixation light source. Thus, locating the visual axis and its intersection with the iris plane is essential for determining the placement of IOLs, since even a slight misalignment may significantly impede their function. Currently, there are no diagnostic devices for accurately and precisely determining the location of the visual axis. Instead, the location of the visual axis through the iris plane is generally approximated to be halfway between the pupil center and the corneal vertex, or first Purkinje image, which is the reflection of a fixation light on the outer surface of the cornea. This method is frequently inaccurate, as the visual axis can be located far away from the aforementioned halfway point, especially in compromised or unusually shaped eyes.

Accordingly, what is needed in the art are improved methods and apparatus for identifying the visual axis of the eye.

SUMMARY

The present disclosure generally relates to methods and apparatus for accurate identification of the visual axis of the eye.

In certain embodiments, a method for determining a location of a visual axis of a patient's eye is provided. The method includes directing a fixation light towards the patient's eye, where the fixation light has two or more fixation light spots formed at different positions along an optical axis of a fixation light source that correspond with two or more images formed on or near a retina of the patient's eye. One or more digital images of an iris plane of the patient's eye are captured by a first camera upon centers of the two or more images formed on or near the retina coinciding in a view of the patient while an optical center of the first camera is aligned with the optical axis of the fixation light source. The location of the visual axis point at the iris plane is then identified based on the one or more digital images, where the location of the visual axis point corresponds with an X/Y location of the optical center of the first camera relative to an X/Y location of the patient's eye as displayed in the one or more digital images.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 3 illustrates a schematic diagram of a visual axis identification system, according to certain embodiments of the present disclosure.

FIGS. 4A and 4B illustrate schematic diagrams of an eye focusing on multiple fixation light points, according to certain embodiments of the present disclosure.

FIGS. 6A and 6B illustrate schematic diagrams of a multiplexer element within a fixation light source, according to certain embodiments of the present disclosure.

FIGS. 15A and 15B illustrate schematic diagrams of an eye focusing on multiple fixation light points generated by the visual axis identification system of FIGS. 3 and 14A-14B, according to certain embodiments of the present disclosure.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to methods and apparatus for identification of the visual axis of the eye.

Typically, the refractive surfaces of an eye, such as the anterior and posterior surfaces of the cornea and lens, are not centered upon the same line (e.g., axis), and the lens is tilted with respect to the eye's gaze. Due to this lack of rotational symmetry, the eye does not have a true optical axis. The eye does, however, have a visual axis, which is the line connecting a fixation target with the fovea of the eye. The center of the eye's field of vision is focused in the fovea where retinal cones are particularly concentrated and thus, visual acuity is highest along the direction of the visual axis. Optical modeling shows that multifocal Lasik treatment should be centered on the visual axis with an accuracy of about 50 μm to avoid the degradation of visual acuity. Therefore, a precise and accurate identification of the eye's visual axis is important for presbyopic Lasik procedures and many other ophthalmic refractive procedures, such as the positioning of multifocal light adjustable lenses.

Presently, there is no device which can accurately identify and locate the visual axis. Rather, medical practitioners, such as ophthalmic surgeons, typically approximate the location of the visual axis through the iris plane as being at a halfway point between the pupil center and the first Purkinje image. This approximation, however, is frequently inaccurate, particularly for compromised or unusually shaped eyes. The devices and methods described herein provide improved methods for accurately identifying and locating the visual axis of the eye and its intersection with the iris plane. The embodiments of the present disclosure may be utilized for corrective lens alignment as well as other ophthalmic procedures, including ophthalmic refractive surgeries such as multifocal LASIK or multifocal PRK surgery.

In one embodiment, a visual axis identification system includes a fixation light source, a camera, and a processing system. During operation thereof, the patient focuses their gaze onto two or more fixation light spots provided by the fixation light source, where the two or more fixation light spots create two or more corresponding images on or near the patient's retina. The patient's head is then rotated while the patient continuously maintains their gaze on the fixation light spots (described in further detail with reference to FIG. 14B). The patient's visual axis may be located by determining the location of the optical axis of the fixation light source relative to the patient's eye when the centers of the multiple images coincide in the patient's field of view.

Figure 1:
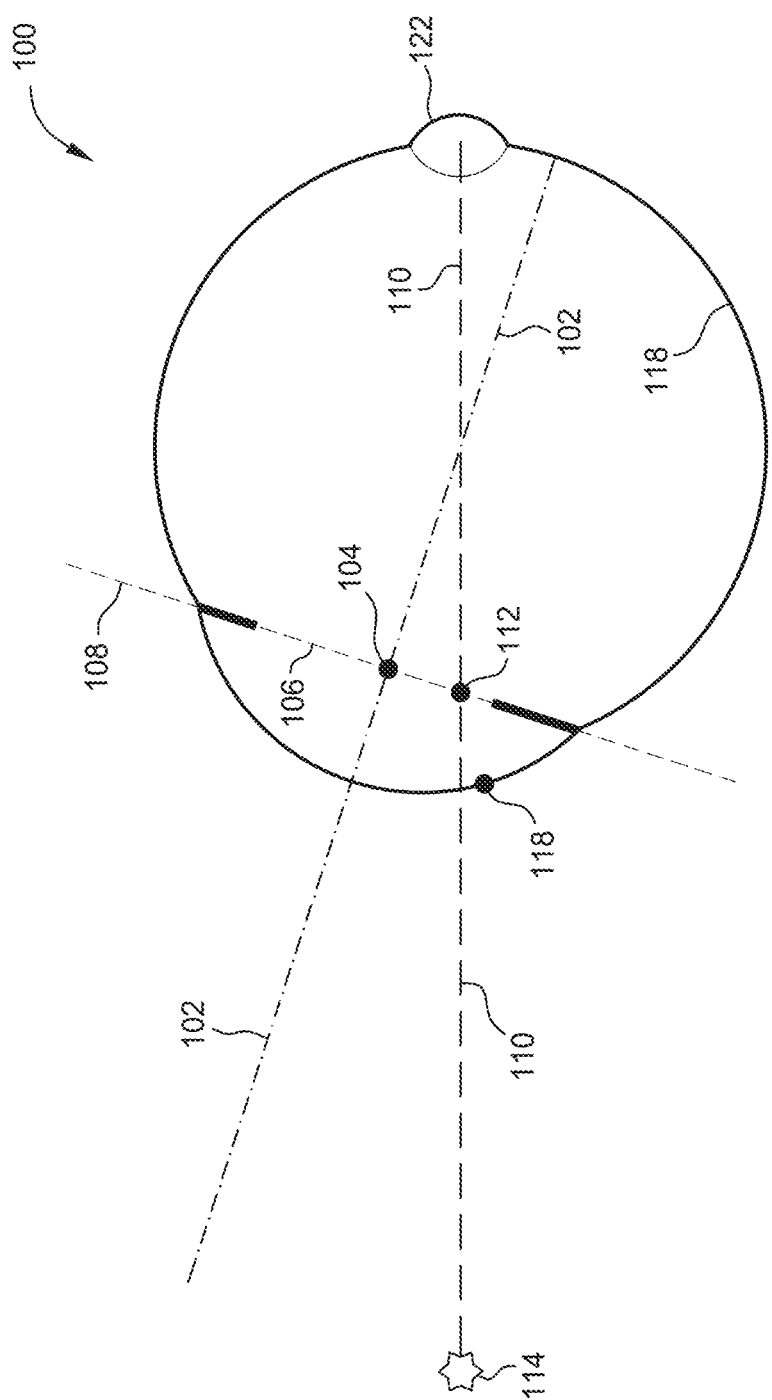
FIG. 1 illustrates a cross-sectional schematic top view of a human eye.

FIG. 1 illustrates a schematic cross-sectional top view of an exemplary human eye 100. The temporal and nasal sides of the eye 100 are depicted in FIG. 1 for reference. As depicted, a pupillary axis 102 passes through a pupil center 104 of pupil 106 and is perpendicular to the pupillary plane 108. The eye 100 further includes a visual axis 110 which intersects with the pupil 106 at a visual axis point 112. The visual axis 110 connects a fixation point 114 (e.g., a fixation target) with the fovea 122, which is a small depression in the retina 116. The center of a field of vision is focused on the fovea 122, and so the sharpest vision of a target is realized when it is in line with the fixation point 114 and the fovea 122. Therefore, accurate determination of the visual axis point 112 is essential for successful ophthalmic corrective procedures. As described earlier, however, there are presently no ophthalmic diagnostic devices that can accurately and precisely identify the visual axis point 112. Rather, conventional ophthalmic techniques involve approximating the visual axis point 112 as halfway between the pupillary center 104 and a corneal vertex 118, or first Purkinje image, which is defined as the location of the specular reflection from an anterior surface of the cornea as seen from the direction of a fixation light source.

Figure 2:
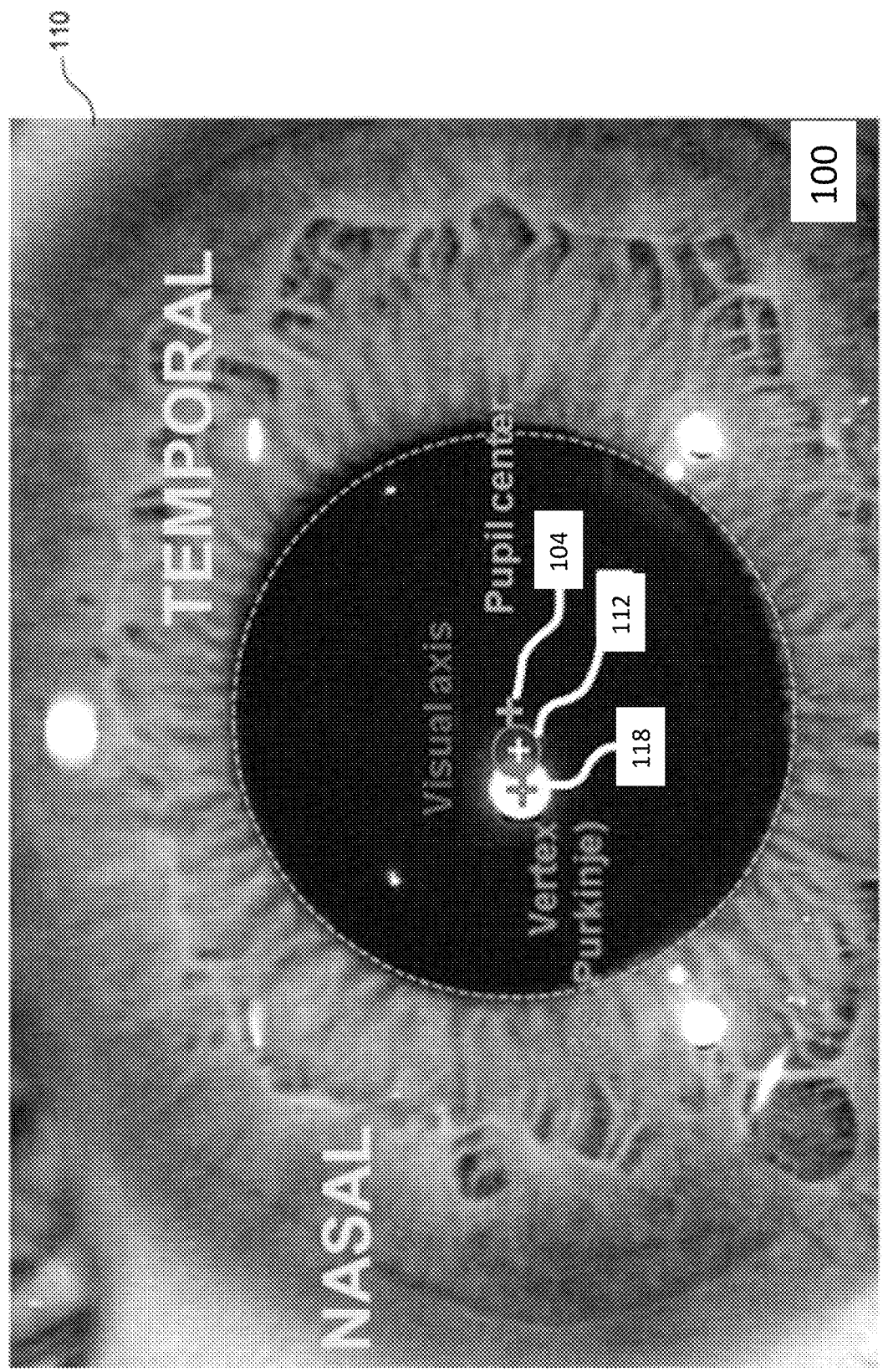
FIG. 2 illustrates a front view of a human eye.

FIG. 2 illustrates a front view of the eye 100 as seen by a clinician (e.g., an ophthalmic surgeon) during the performance of a procedure. In FIG. 2, the visual axis point 112 is assumed to be located halfway between the pupil center 104 and the corneal vertex 118. However, the visual axis point 112 is frequently not halfway between the pupil center 104 and the corneal vertex 118, particularly in asymmetrical, irregular, or comprised eyes. Thus, approximation of the location of the visual axis point 112 can be inaccurate, imprecise, and unreliable, and can lead to suboptimal presbyopic Lasik or PRK treatments.

FIG. 3 illustrates a simplified schematic view of an exemplary visual axis identification system 300 according to some embodiments. The visual axis identification system 300 is utilized to accurately and precisely determine the visual axis point 112 of the visual axis 110 of the eye 100. Generally, the visual axis identification system 300 includes a fixation light source 302, a camera 304, and a processing system 306.

The fixation light source 302 is configured to form two or more fixation light spots $P_N$ (e.g., fixation points, shown in FIGS. 4A and 4B) along an optical axis 312 thereof upon which the patient's eye, represented by the eye 100, can focus during utilization of the visual axis identification system 300. In operation, the patient focuses on the two or more fixation light spots $P_N$ and attempts to visually align them by moving their head. Alignment or overlap of the fixation light spots $P_N$ occurs when the visual axis 110 of the eye 100 and the optical axis 312 of the fixation light source 302 coincide. Thus, upon alignment, the visual axis point 112 may be identified. To generate light, the fixation light source 302 may include any suitable light-emitting devices, including light emitting diodes (LEDs), filament lamps, and the like. In certain embodiments, the generated light is concentrated into two or more fixation light spots $P_N$ by a multiplexer 320 and then relayed by a relay lens 322 along the optical axis 312.

In certain embodiments, the visual axis identification system 300 further includes an optical relay device 310 along the optical axis 312 for relaying the fixation light spots $P_N$ to the eye 100 and/or manipulating the propagation path of the optical axis 312. For example, the optical relay device 310 may be utilized to align the optical axis 312 of the fixation light source 302 with an optical axis 314 of the camera 304. Examples of suitable types of optical relay devices include relay lenses, beam splitters, filters, and the like. Although one optical relay device 310 is depicted, the utilization of two or more optical relay devices 310 is also contemplated.

The camera 304 may include any suitable type of digital imaging device or detector, such as an eye tracking camera or similar optical sensor, for capturing images of and determining the position (e.g., X/Y translational position) of the eye 100. Generally, the camera 304 is configured to record images or video of the iris plane of the eye 100 while the patient is focusing on the fixation light spots $P_N$ formed by the fixation light source 302. The images or video are then transmitted to the processing system 306 for analysis to determine the relative X/Y location of the eye 100 and the visual axis point 112 thereof. In certain embodiments, the camera 304 is an infrared camera. In certain embodiments, the camera 304 is configured to track movement of the eye 100 and in particular, the pupil center 104, by mapping and detecting shifts (e.g., movement) in the vasculature (e.g., blood vessels) within the eye 100, such as the scleral veins. The camera 304 is communicatively coupled to the processing system 306 and, in certain embodiments, forms a single device therewith. In certain other embodiments, the camera 304 and the processing system 306 may be separate devices or components of the visual axis identification system 300.

Figure 5B:
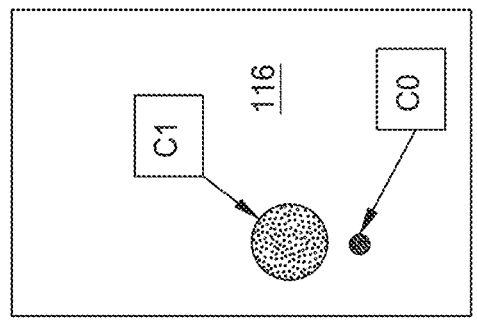
FIGS. 5A and 5B illustrate schematic diagrams of an eye focusing on multiple fixation light points, according to certain embodiments of the present disclosure.
Figure 5A:
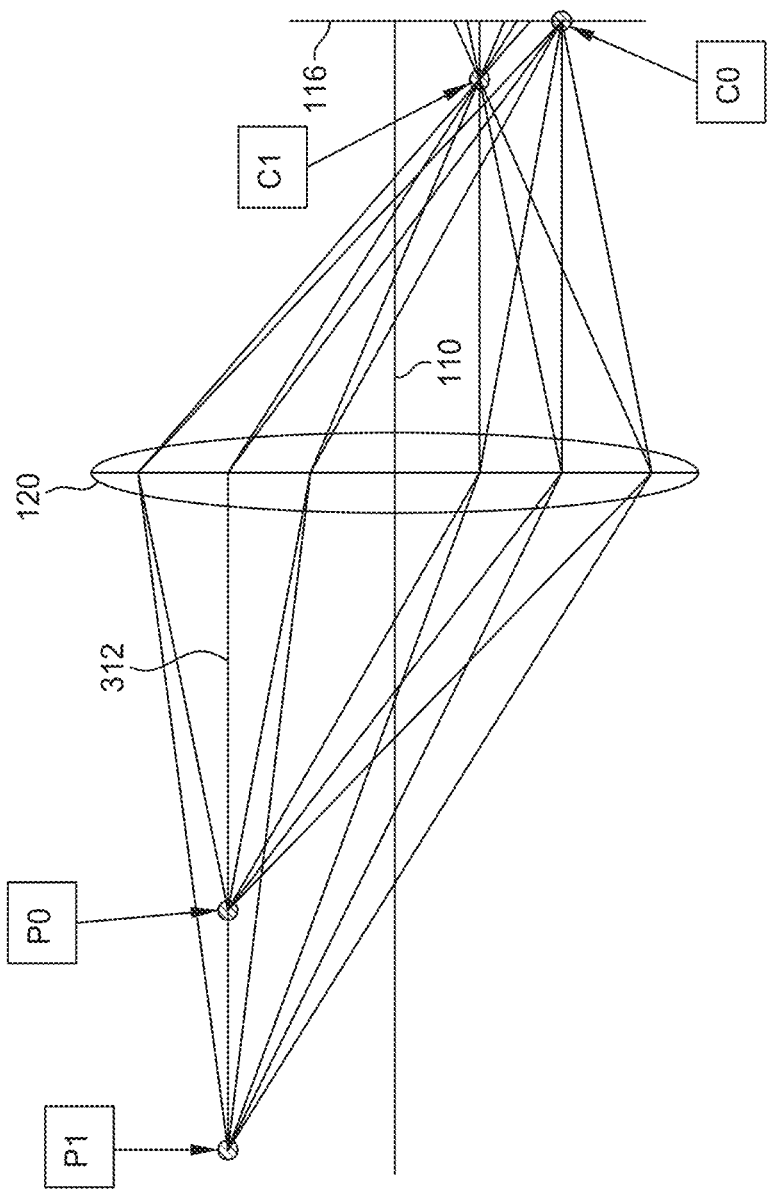

To illustrate example operations of the visual axis identification system 300, FIGS. 4A-4B and 5A-5B depict simplified schematic diagrams of the eye 100 focusing on two fixation light spots $P_1$ and $P_0$. FIGS. 4A and 5A schematically illustrate the image formation of fixation light spots $P_1$ and $P_0$ in the eye 100, while FIGS. 4B and 5B illustrate the corresponding images $C_1$ and $C_0$ formed on retina 116. Imaging system 120 represents the image forming components of the eye such as the cornea having a typical refractive power of about 43 diopter and the natural lens having a typical refractive power of about 17 diopter. As described above, the fixation light source 302 is configured to generate and concentrate light into at least two fixation light spots $P_1$ and $P_0$ aligned on the optical axis 312 thereof. According to the example shown in FIG. 4A, the fixation light spot $P_0$ is imaged onto the retina 116 while the fixation light spot $P_1$ is imaged just short (e.g., slightly in front of) of the retina 116. This results in the image $C_0$ appearing small and sharp to the patient and the image $C_1$ appearing larger and less sharp (e.g., more blurred) than image $C_0$.

As depicted in FIGS. 4A and 4B, when the optical axis 312 of the fixation light source 302 (shown in FIG. 3) coincides with the visual axis 110 of the patient's eye 100, the centers of images $C_1$ and $C_0$ coincide on the retina 116. Therefore, the patient visualizes the small and sharp image $C_0$ as centrally aligned or overlaid with the large and blurred image $C_1$, shown in FIG. 4B. However, when the optical axis 312 and the visual axis 110 do not coincide, the images $C_1$ and $C_0$ are spatially shifted relative to each other, as depicted in FIGS. 5A and 5B. Thus, both $C_1$ and $C_0$ are seen by the patient, albeit with unaligned or non-coinciding centers as shown in FIG. 5B. Utilizing this principle, the location of the visual axis point 112 can then be identified by, in certain embodiments, having the patient move or adjust their head up and down or left and right while maintaining their gaze on the fixation light spots $P_1$ and $P_0$ until the patient visualizes centrally aligned or overlaid images $C_1$ and $C_0$, thereby indicating alignment of the visual axis 110 with the optical axis 312 of the fixation light source 302. A more detailed description of the patient's head movement is found below with reference to FIG. 14B.

FIGS. 6A and 6B illustrate simplified schematic diagrams of the multiplexer 320 and relay lens 322 of the fixation light source 302 forming two or more fixation light spots, according to certain embodiments of the present disclosure. As previously described, the fixation light spots generated by the multiplexer 320 are observed by the patient during operation of the visual axis identification system 300 using the relay lens 322. As further described above, the visual alignment of the fixation light spots can be utilized to locate the visual axis point 112 of the patient. While FIGS. 6A and 6B are illustrative of the function of the multiplexer 320, specific examples or types of multiplexers are described in further detail below with reference to FIGS. 7-13B.

In FIG. 6A, the multiplexer 320 is a spot doubler and concentrates incoming light 602 into two fixation light spots $P_1$ and $P_0$ on optical axis 312. In FIG. 6B, the multiplexer 320 is a spot multiplexer and concentrates the incoming light 602 into three fixation light spots $P_2$, $P_1$, and $P_0$. Though only three fixation light spots are shown in FIG. 6B, it is contemplated that the multiplexer 320 may generate more than three fixation light spots. In certain embodiments, increasing the number of fixation light spots increases the accuracy of the visual identification system 300. In either example depicted, the fixation lights spots generated by the multiplexer 320 are observed by the patient through the relay lens 322, which serves at least two functional purposes: firstly, the relay lens 322 relays the fixation light spots to the eye 100 (e.g., like a magnifying glass); secondly, the relay lens 322 compensates for the refractive error of the eye 100 to make the fixation light spots appear sharp to the patient (e.g., functions as a Badal system).

As previously described, FIGS. 7-13B illustrate specific examples of multiplexers 320 than can be utilized to concentrate light within the fixation light source 302 into two or more fixation light spots on an optical axis thereof, such as optical axis 312. The fixation light spots formed by the multiplexers 320 are observed by the patient, who attempts to align the fixation spots to help the visual axis identification system 300 with identifying the visual axis point 112.

Figure 8:
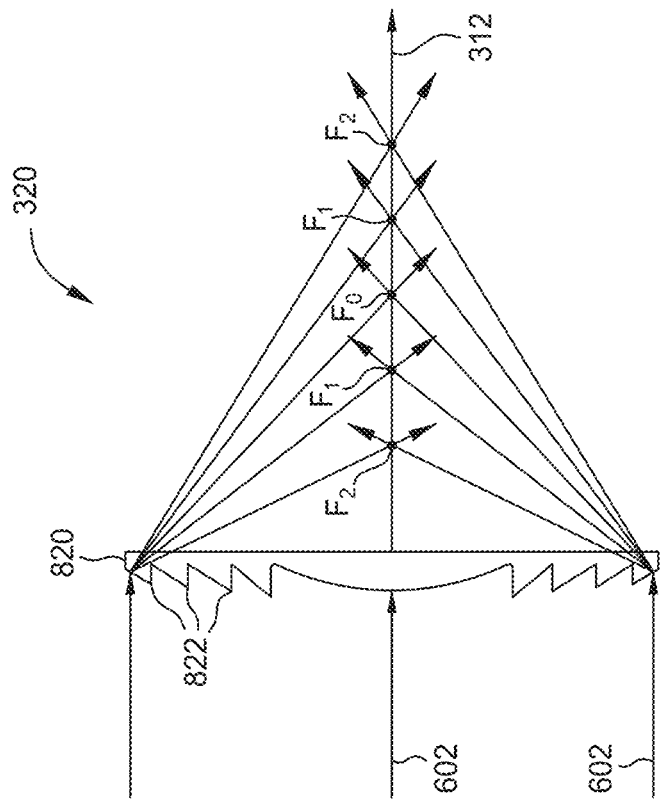
FIG. 8 illustrates a schematic diagram of an exemplary multiplexer element that can be used in combination with the visual axis identification system of FIG. 3, according to certain embodiments of the present disclosure.
Figure 7:
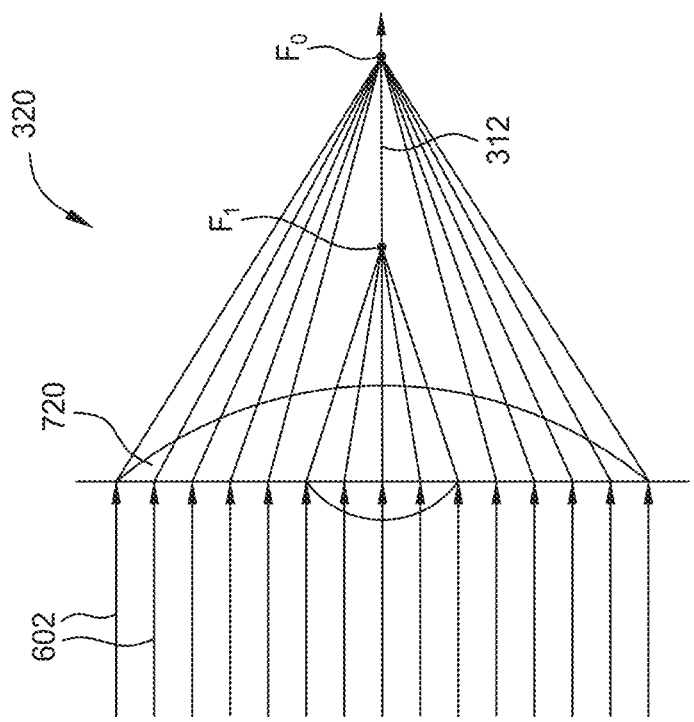
FIG. 7 illustrates a schematic diagram of an exemplary multiplexer element that can be used in combination with the visual axis identification system of FIG. 3, according to certain embodiments of the present disclosure.

In the example depicted in FIG. 7, the multiplexer 320 is a bifocal lens 720 having two focal points $F_0$ and $F_1$ at which light 602 is concentrated. The concentration of light 602 at these two focal points $F_0$ and $F_1$ results in the generation of two fixation light spots on optical axis 312 that are relayed towards the patient's eye, as described with reference to FIG. 4A. In another example depicted in FIG. 8, the multiplexer 320 is a multifocal diffractive lens 820. The multifocal diffractive lens 820 includes one or more features 822 or properties configured to focus light 602 at multiple focal points in different diffraction orders on optical axis 312. As depicted in FIG. 8, the multifocal diffractive lens 820 focuses light 602 at five different focal points including the zero order focus $F_0$, as well as higher order foci $F_1$, $F_2$, $F_{-1}$, and $F_{-2}$. Each of the focal points $F_0$, $F_1$, $F_2$, $F_{-1}$, and $F_{-2}$ corresponds with a fixation light spot that can be observed by the patient. Although five focal points are shown, it is contemplated that the multifocal diffractive lens 820 may form less than five or more than five focal points. In certain embodiments, the multifocal diffractive lens 820 is a Fresnel-type lens. In certain other embodiments, the multifocal diffractive lens 820 is a holographic lens or diffractive optical element formed by holographic or lithographic techniques.

Figure 9:
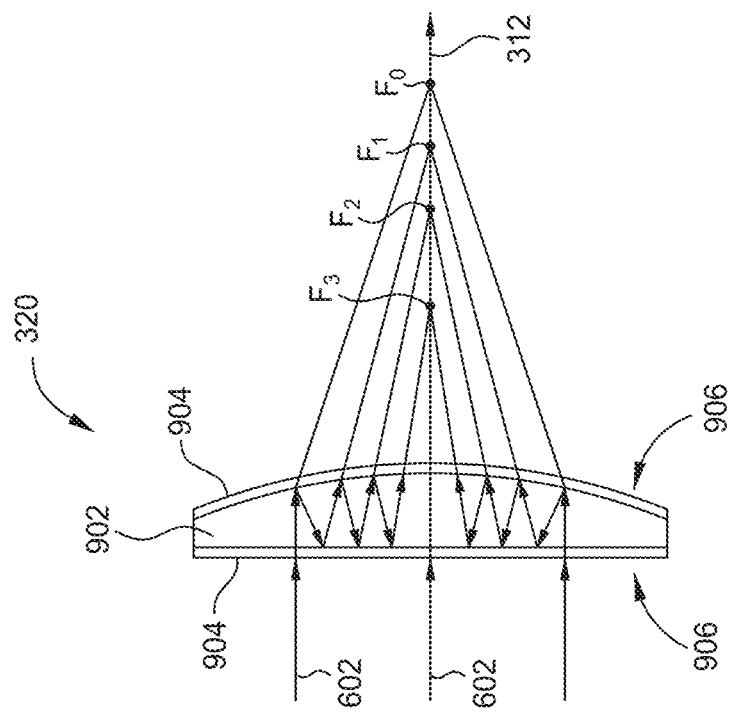
FIG. 9 illustrates a schematic diagram of an exemplary multiplexer element that can be used in combination with the visual axis identification system of FIG. 3, according to certain embodiments of the present disclosure.

FIG. 9 illustrates another example of a multiplexer 320 that can be utilized in fixation light source 302. The multiplexer 320 in FIG. 9 is a lens 902 having coatings 904 on both major surfaces 906. The coatings 904 are partially reflective and partially transparent, and thus, light 602 is both reflected and transmitted by the coatings 904 to form multiple focal points. When an incident beam of the light 602 is parallel and centered on the optical axis 312, the multiple focal points formed by the lens 902 coincide with the optical axis 312. As depicted, the focal point $F_0$ is the resulting focal point from a condition where light 602 is transmitted through the lens 902 without any internal reflections thereof. The focal point $F_1$, however, results from two internal reflections by the coatings 904. The focal points $F_2$ and $F_3$ result from four and six internal reflections, respectively. The focal points $F_0$, $F_1$, $F_2$, and $F_3$ are formed at different locations on optical axis 312 as a result of at least one of the major surfaces 906 being curved, causing different reflective angles and/or reflective powers.

In certain embodiments, the coatings 904 enable spectral separation of the light 602. For example, the reflectivity peak (e.g., maximum reflectivity) of the coatings 904 may correspond with the wavelength of the light 602 to be visualized by the patient. In another example, the coating 904 may have zero reflectivity at a wavelength of the light 602 to be detected by the camera 304. Accordingly, undesired reflection of the light 602 toward the camera 304 may be eliminated or significantly reduced by the coatings 904.

Figure 10:
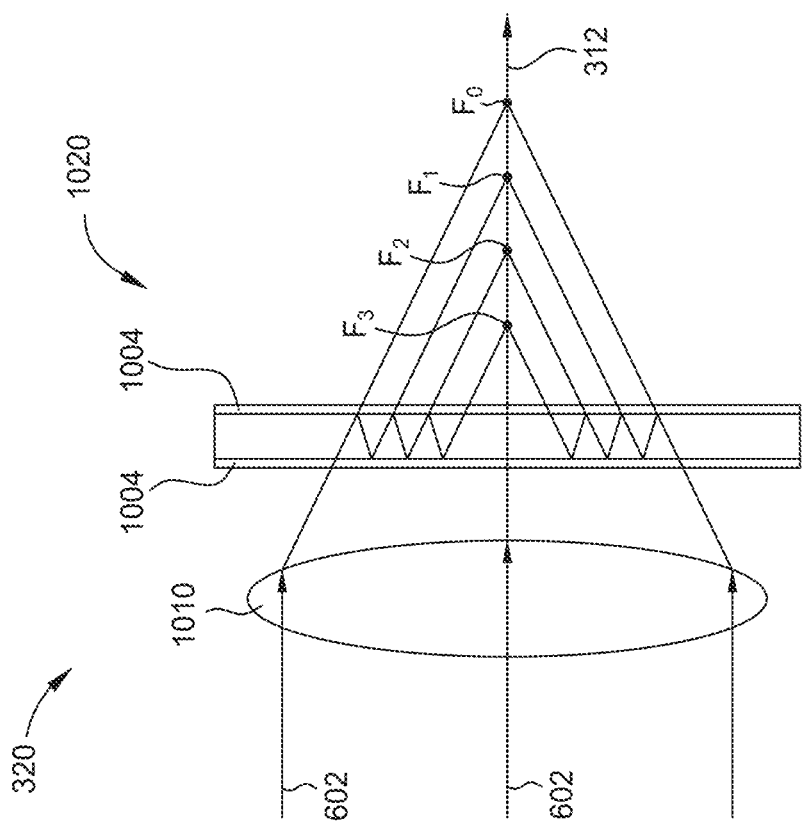
FIG. 10 illustrates a schematic diagram of an exemplary multiplexer element that can be used in combination with the visual axis identification system of FIG. 3, according to certain embodiments of the present disclosure.

In FIG. 10, the exemplary multiplexer 320 is a Fabry-Perot interferometer (FPI) 1020 having two parallel and semitransparent (e.g., partially reflective) mirrors 1004 in combination with a convex focusing lens 1010. The convex focusing lens 1010 focuses parallel beams of light 602 onto the FPI 1020, which then internally reflects and/or transmits the light to form several focal points on optical axis 312. Four focal points $F_0$, $F_1$, $F_2$, and $F_3$ are depicted in FIG. 10, although more or less are contemplated. The first focal point $F_0$ is a result of light 602 being transmitted through the FPI 1020 without any internal reflection thereof. The focal points $F_1$, $F_2$, and $F_3$, however, are a result of two reflections, four reflections, and six reflections, respectively.

Figure 11:
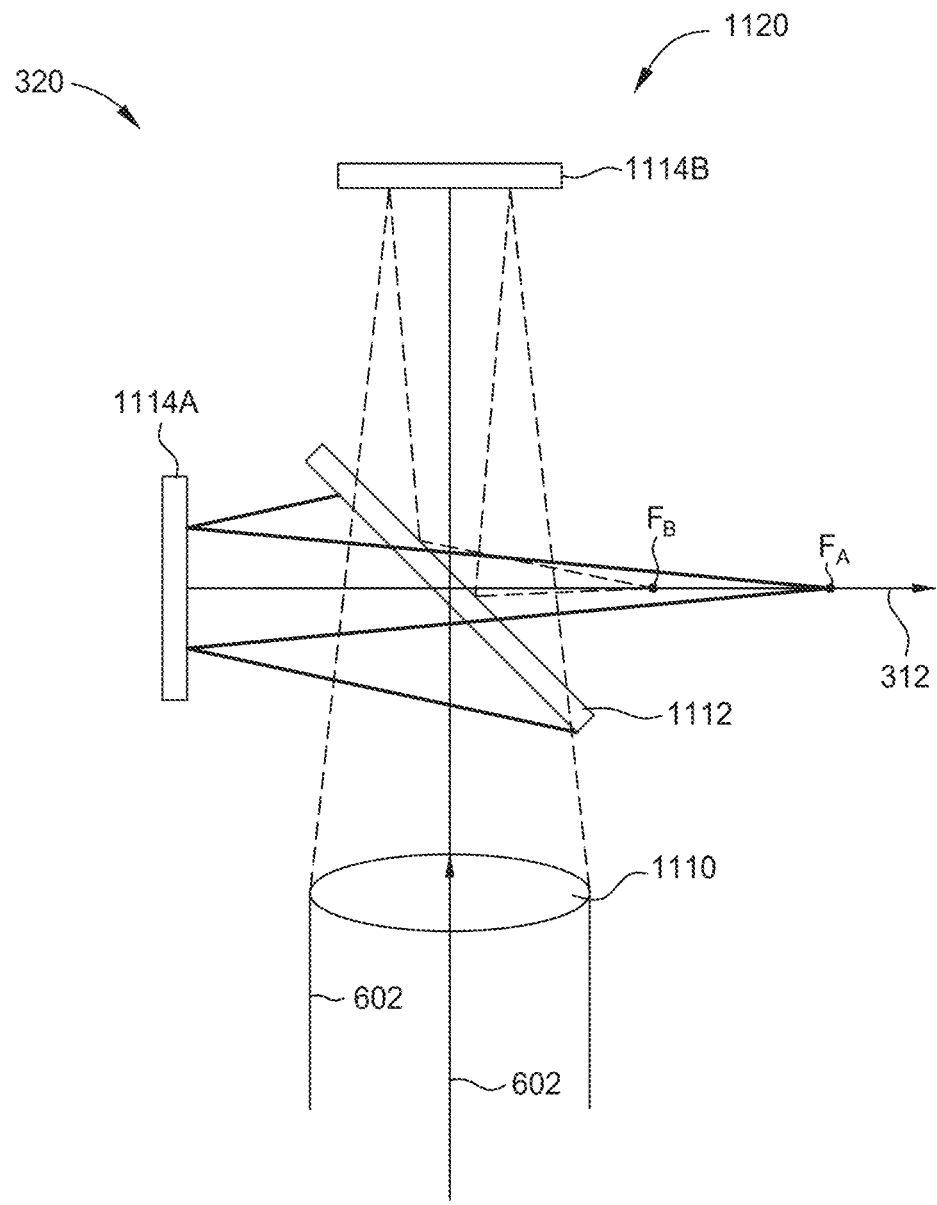
FIG. 11 illustrates a schematic diagram of an exemplary multiplexer element that can be used in combination with the visual axis identification system of FIG. 3, according to certain embodiments of the present disclosure.

In another example depicted in FIG. 11, the multiplexer 320 is an interferometer 1120. In particular, FIG. 11 depicts a Michelson-type interferometer 1120 having two peripheral and fully reflective mirrors 1114A and 1114B and a semitransparent (e.g., partially reflective) central mirror 1112. Each of the peripheral mirrors 1114A and 1114B is disposed at a different distance (e.g., arm length) from the central mirror 1112. As shown, the central mirror 1112 reflects a portion of incoming light 602 to peripheral mirror 1114A and transmits another portion of light 602 to peripheral mirror 1114B. Upon reflection by the mirrors 1114A and 1114B, the light 602 is once again reflected or transmitted through central mirror 1112 disposed along the optical axis 312. The different arm lengths of peripheral mirrors 1114A and 1114B causes the light 602 reflected from each mirror to focus at different focal points along the optical axis 312, depicted as focal points $F_A$ and $F_B$. In certain embodiments, the interferometer 1120 is optically coupled with a convex focusing lens 1110 to focus light 602 onto the central mirror 1112. Further, although the interferometer 1120 is depicted as a Michelson-type interferometer, any suitable type of interferometer may be utilized as the multiplexer 320. For example, the interferometer 1120 may be a Mach-Zehnder, Twyman-Green, or Gires-Tournois interferometer in certain embodiments.

Figure 12:
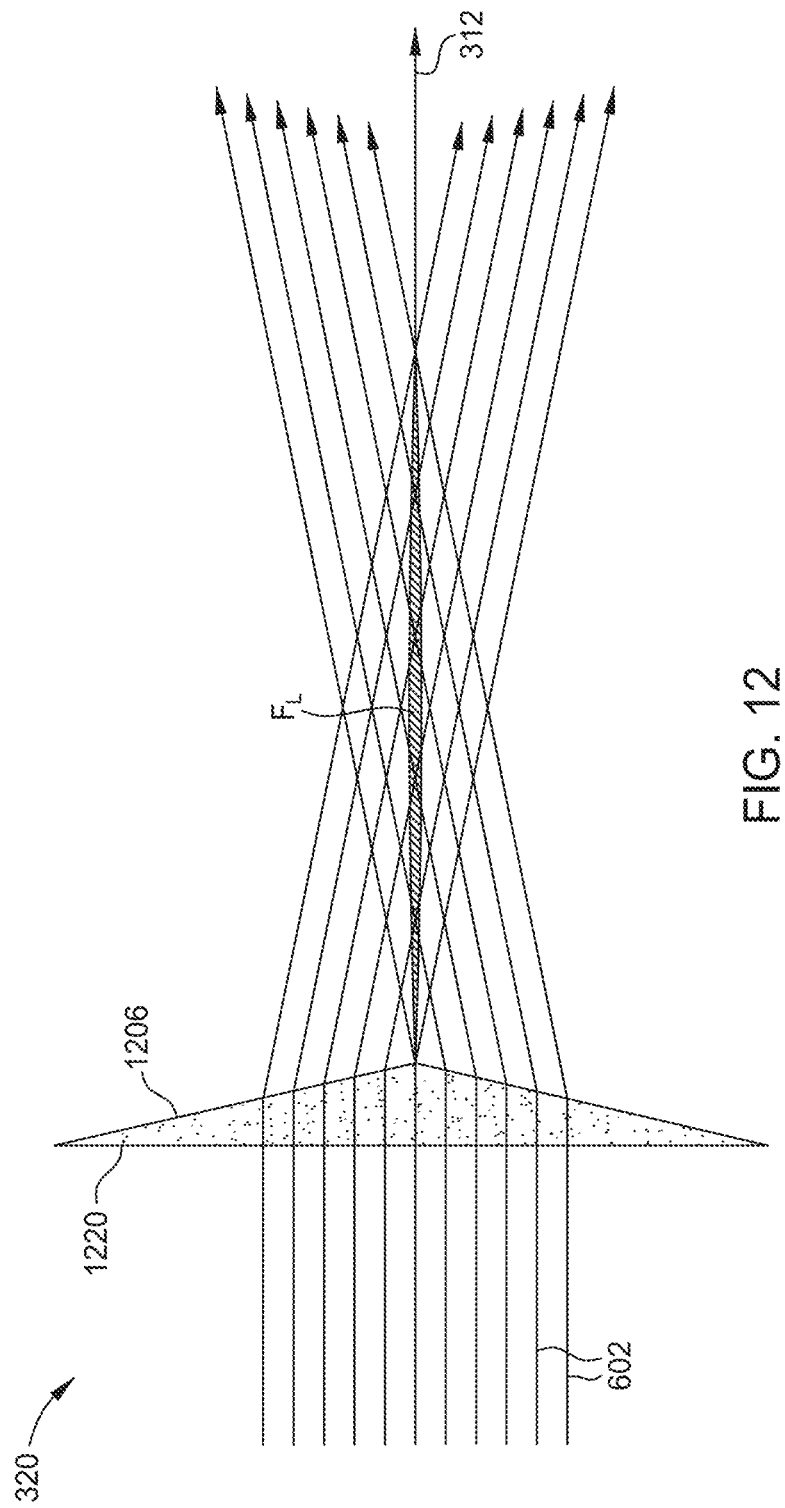
FIG. 12 illustrates a schematic diagram of an exemplary multiplexer element that can be used in combination with the visual axis identification system of FIG. 3, according to certain embodiments of the present disclosure.
Figure 13B:
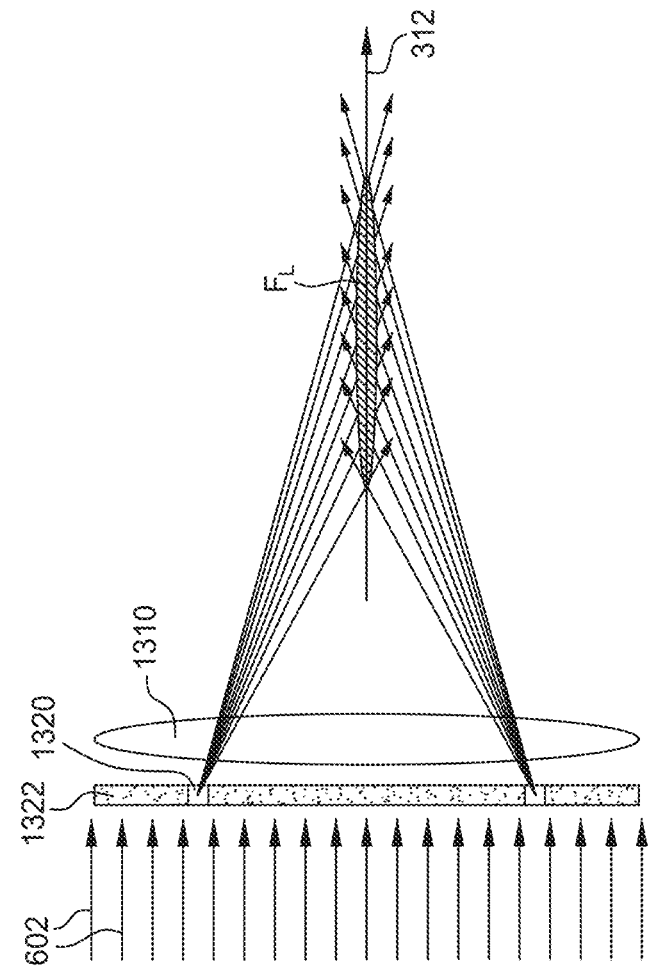
FIGS. 13A and 13B illustrate schematic diagrams of an exemplary multiplexer element that can be used in combination with the visual axis identification system of FIG. 3, according to certain embodiments of the present disclosure.
Figure 13A:
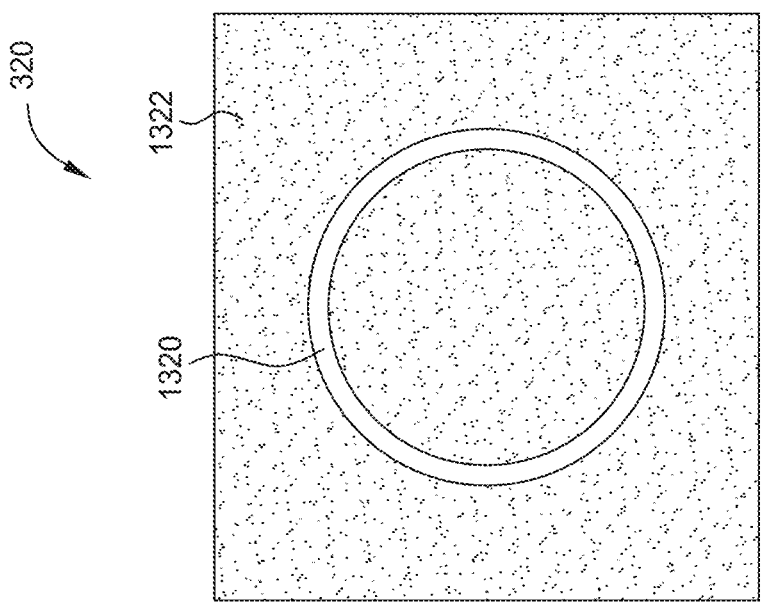

FIGS. 12, 13A, and 13B illustrate examples of multiplexers 320 configured to generate Bessel beams (e.g., non-diffracting beams). Bessel beams have extremely long focal lines, which can be interpreted as many multiplexed focal points where the focal points overlap in depth. In operation, a patient views the fixation light spot formed by the Bessel beam and rotates their head to align the Bessel beam with their visual axis 110 so that the Bessel beam appears as a single spot. Upon visualization of the Bessel beam as a single spot, the visual axis point 112 of the patient can be located.

In the example of FIG. 12, the multiplexer 320 is an axicon 1220 having at least one conical and refractive surface 1206. The conical surface 1206 has a rotational symmetry around the optical axis 312 and thus, refracts light 602 into intersecting beams (e.g., a Bessel beam) forming a very long focal line $F_L$ on the optical axis 312.

In another example of a Bessel beam generator, FIGS. 13A and 13B depict a front planar view and a side schematic view of an annular ring (e.g. annular aperture) 1320 formed in a screen 1322. When the annular ring 1320 is axially aligned with a convex focusing lens 1310, light 602 passes through the annular ring 1320 and is focused by the convex focusing lens 1310 to form focal line $F_L$ along the optical axis 312, similar to the axicon 1220. In still further examples, the multiplexer 320 may also include a diffractive or holographic optical element configured to generate a Bessel beam.

Figure 14A:
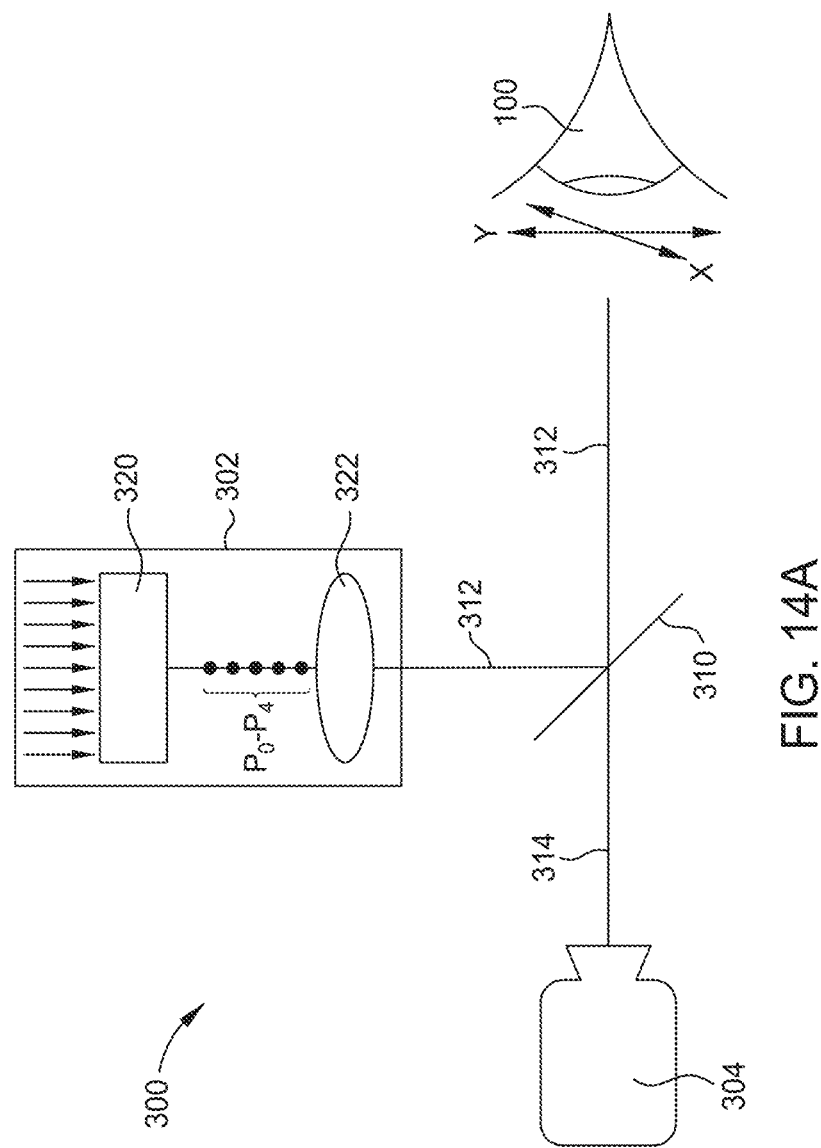
FIGS. 14A and 14B illustrate schematic diagrams of the visual axis identification system of FIG. 3, according to certain embodiments of the present disclosure.
Figure 14B:
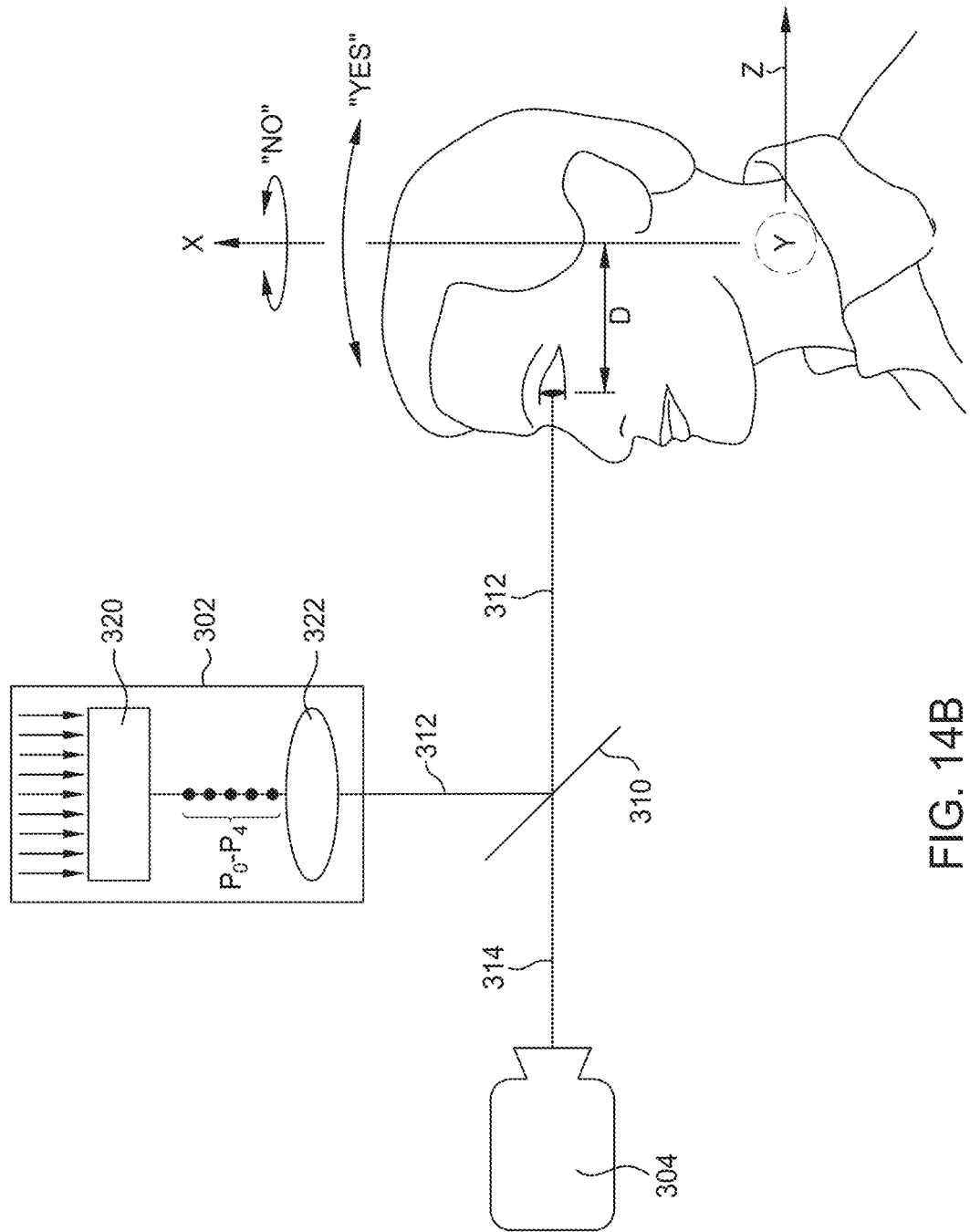

As described above, the different multiplexers, shown in FIGS. 7-13B, may be used in a visual axis identification system, such as the visual axis identification system 300 of FIG. 3. FIGS. 14A and 14B illustrate slightly simplified versions of the visual axis identification system 300 of FIG. 3, and example operations of the visual axis identification system 300 are described herein with more detail with respect to FIGS. 14A and 14B. As depicted, fixation light spots $P_0$-$P_4$ are generated by the multiplexer 320 (e.g., which may be one of the multiplexers of FIGS. 7-13B) of the fixation light source 302 and relayed onto the optical axis 312 by the relay lens 322. The optical axis 312 is directed towards the patient's eye 100 by utilizing one or more optical relay devices 310. As the patient continuously fixates his or her gaze on the fixation light spots $P_0$-$P_4$, the patient rotates his or her head in a "yes" (e.g., rotation about the Y axis) and/or "no" (e.g., rotation about the X axis) movement until the fixation light spots $P_0$-$P_4$ appear as being centrally coinciding or aligned. When alignment of the corresponding images $C_0$-$C_4$ (shown in FIGS. 15A and 15B) of the fixation light spots $P_0$-$P_4$ occurs, the optical axis 312 is aligned with the visual axis 110 of the patient's eye 100.

FIG. 14B also depicts how the "no" movement of the head results in a shift of the eye 100 along a lateral direction or plane. For example, if the distance D between the cornea and the vertical anatomical rotation axis X of the head is 80 mm, rotation of the head around the vertical rotation axis X (i.e., "no" movement) by 1° will result in a 80 mm*sin(1°)=1.4 mm shift of the eye 100 in a lateral direction.

Simultaneously with the rotational movement of the patient's head, camera 304 captures images or video of the iris plane of eye 100 from a direction along which the light generated by the fixation light source 302 travels to the eye 100. In certain embodiments, the optical axis 314 of the camera 304 is aligned with the optical axis 312 of the fixation light source 302 and therefore, is also aligned with the visual axis 110 of the patient's eye 100 when the patient observes centrally coinciding or aligned images $C_0$-$C_4$ of the fixation spots $P_0$-$P_4$. Accordingly, at the point at which the patient observes coinciding images $C_0$-$C_4$ of the fixation light spots $P_0$-$P_4$, the optical center of the camera 304 (which has an optical axis 314 aligned with optical axis 312 of the fixation light source 302) corresponds to the visual axis point 112 of the eye 100. In certain embodiments, the optical center of the camera 304 is marked on the captured images or video, or on a display screen observed by the user (e.g., surgeon).

Once the patient achieves alignment of the fixation light spots $P_0$-$P_4$, the patient retains their position to maintain the alignment while the camera 304 captures images of the eye 100 to locate the visual axis point 112, corresponding with the optical center of the camera 304. In certain embodiments, a video or series of images is captured by the camera 304 over a desired amount of time while the patient maintains alignment of the images $C_0$-$C_4$ fixation light spots $P_0$-$P_4$. In certain embodiments, the video (which comprises a series of images) or series of images captured by the camera 304 is analyzed by the processing system 306 (not shown in FIGS. 14A and 14B) to determine an average X/Y location of the optical center of the camera 304 in relation to the X/Y position of the eye 100, thereby averaging out any unintended eye and/or head movement by the patient when observing the fixation light spots $P_0$-$P_4$. The average X/Y location of the optical center of the camera 304 corresponds to the visual axis point 112 of the eye 100. The determined average X/Y location of the optical center of the camera 304 in relation to the X/Y position of the eye 100 corresponds to the average of all X/Y locations of the optical center of the camera 304 in the series of images or video, described in further detail below with reference to FIG. 16.

FIGS. 15A and 15B illustrate schematic diagrams of eye 100 observing the multiple fixation light points $P_0$-$P_4$ generated by the multiplexer 320 in FIGS. 14A and 14B. As depicted in FIG. 15A, when all of the fixation light spots $P_0$-$P_4$ are aligned with the visual axis 110 of the patient's eye 100, the fixation light spots $P_0$-$P_4$ form coinciding images $C_1$-$C_4$ on the retina 116. The patient may achieve such alignment by moving his or her head in a "yes" or "no" movement about the X and/or Y axes while continuously maintaining focus on the fixation light spots $P_0$-$P_4$, as described above and shown in FIG. 14B. Upon alignment, the patient attempts to hold their position so that camera 304 can capture images or video of the position of the eye 100 relative to the optical center of the camera 304. When the fixation light spots $P_0$-$P_4$ (and optical axis 312) are unaligned with the visual axis 110, as depicted in FIG. 15B, the fixation light spots $P_0$-$P_4$ form spatially shifted images $C_0$-$C_4$ on the retina 116, and the patient must adjust the position of their head.

Figure 16:
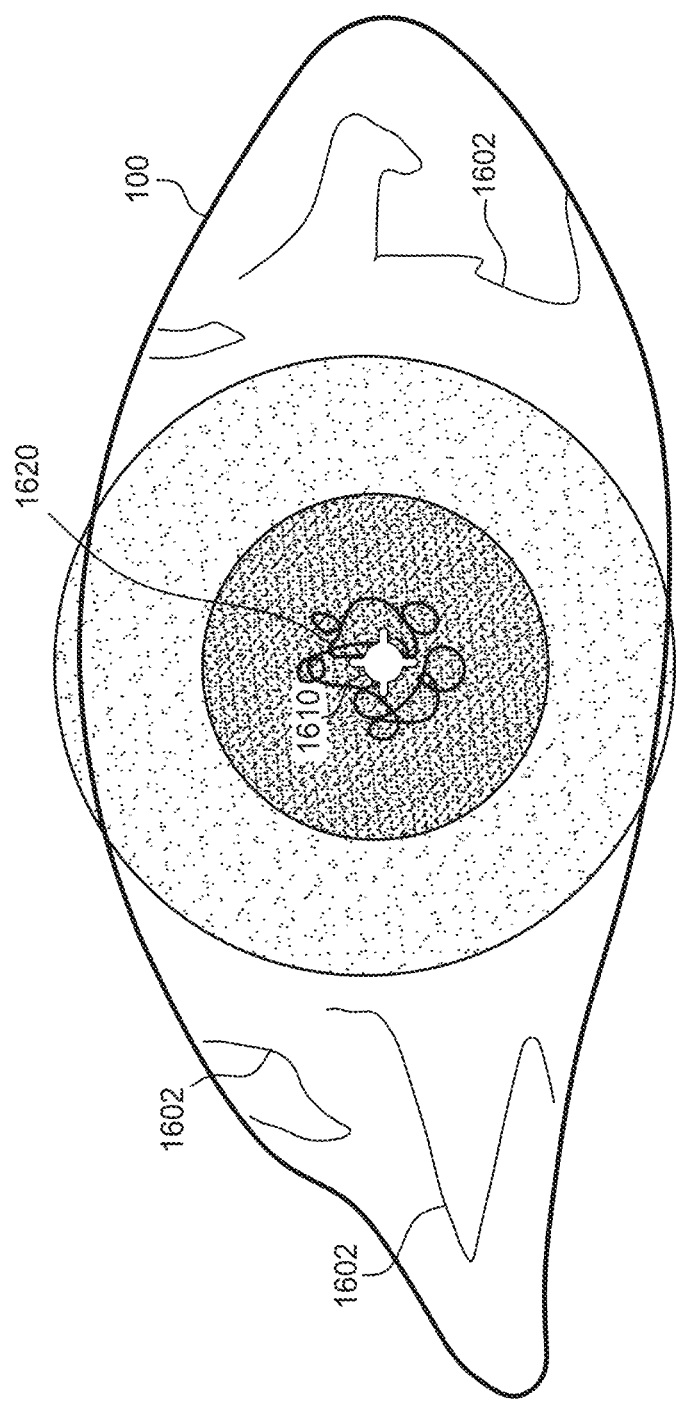
FIG. 16 illustrates a front view image of an eye as generated by a camera during the method of using the visual axis identification system of FIG. 3, according to certain embodiments of the present disclosure.

FIG. 16 illustrates a front view image of eye 100 during the use of the visual axis identification system of FIGS. 3 and 14A-14B, according to certain embodiments of the present disclosure. The view depicted in FIG. 16 may be that of camera 304, which can be displayed on a display screen for observation by the surgeon. As shown, a trace 1610 shows the history of the location of the optical axis 312 of the fixation light source 302 on the iris plane of the eye 100, and a marker 1610 designates a center of gravity of the trace 1620. During operation, the optical center of the camera 304 is configured to coincide with the optical axis 312 of the fixation light source 302. The location of the optical center of the camera 304 (and thus, the optical axis 312) is tracked by the trace 1620 in images or video captured while the patient observes centrally aligned fixation spots. The trace 1620 is then analyzed to determine the X/Y position of the marker 1610 designating the center of gravity of the trace 1620 relative to the X/Y position of the eye 100, which corresponds with the "average" visual axis point 112. In certain embodiments, the relative X/Y positioning of the marker 1610 and eye 100 is determined by mapping and tracking of scleral veins 1602.

Figure 17A:
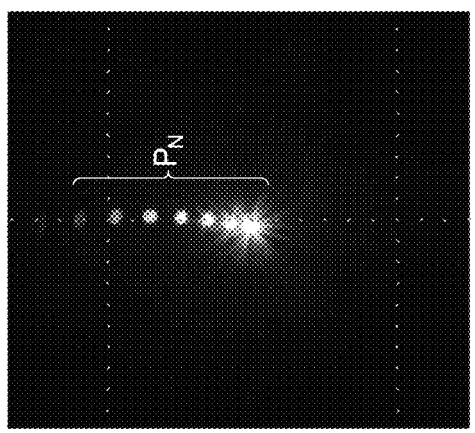
FIGS. 17A-17E illustrate representations of a patient's field of view during use the visual axis identification system of FIGS. 3 and 14A-14B, as well as a system for generating the aforementioned representations, according to certain embodiments of the present disclosure.
Figure 17B:
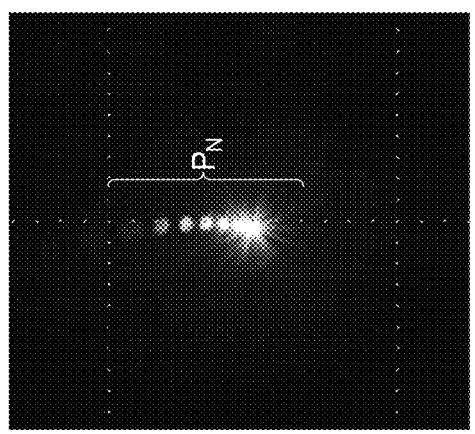
Figure 17C:
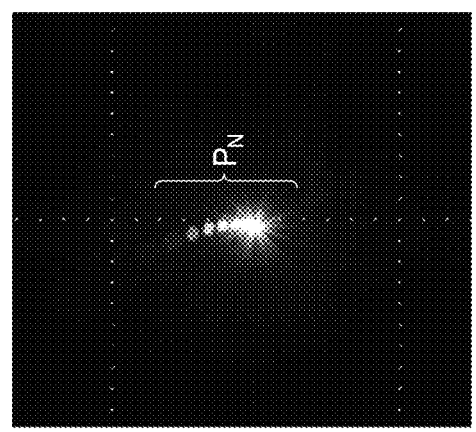
Figure 17D:
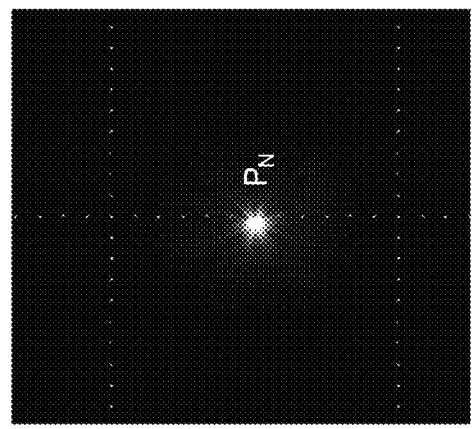
Figure 17E:
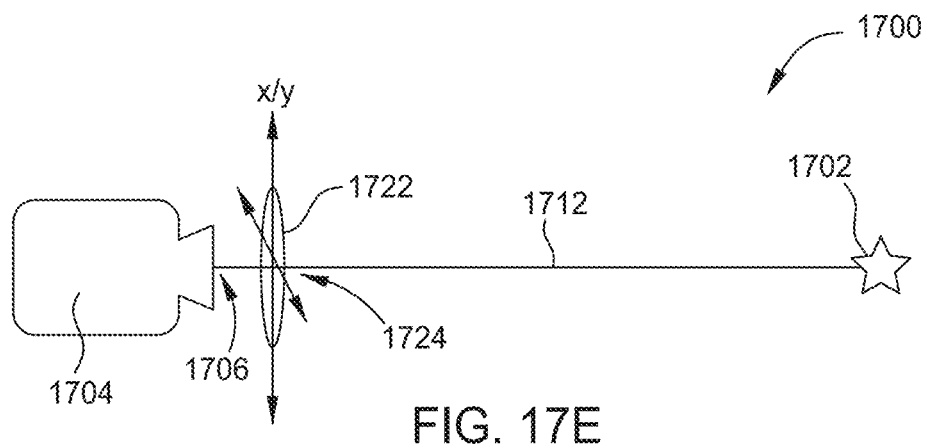

FIGS. 17A-17D illustrate representations of the patient's viewing field when observing fixation light spots $P_N$ formed by the fixation light source 302. As shown in FIGS. 17A-17C, when the optical axis 312 and the visual axis 110 are unaligned, the patient visualizes a somewhat linear progression of fixation light spots $P_N$ that progresses in both size and sharpness. However, upon alignment of the axes 312 and 110, the fixation light spots spatially coincide or overlap, as shown in FIG. 17D. FIG. 17E illustrates a system 1700 utilized to obtain the representations described above. The system includes a point-like fixation light source 1702 to generate a fixation light, a coated lens 1722 to focus the fixation light into two or more fixation light spots, and a camera 1704 for capturing images of fixation light spots focused by the coated lens 1722. When the optical center 1706 of the camera 1704, an optical center 1724 of the coated lens 1722, and an optical axis 1712 of the fixation light source 1702 coincide, the camera 1704 captures images similar to that of FIG. 17D. These circumstances represent the scenario where a patient's visual axis 110 coincides with the optical axis 312 of the fixation light source 302. When the optical center 1724 of the coated lens 1722 is spatially (e.g., X or Y direction) shifted with respect to the optical axis 1712 and/or optical center 1706 of the camera 1704, the camera 1704 captures images similar to those of FIGS. 17A-17C. These circumstances represent the scenario where a patient's visual axis 110 is spatially shifted with respect to the optical axis 312 of the fixation light source 302.

Figure 18:
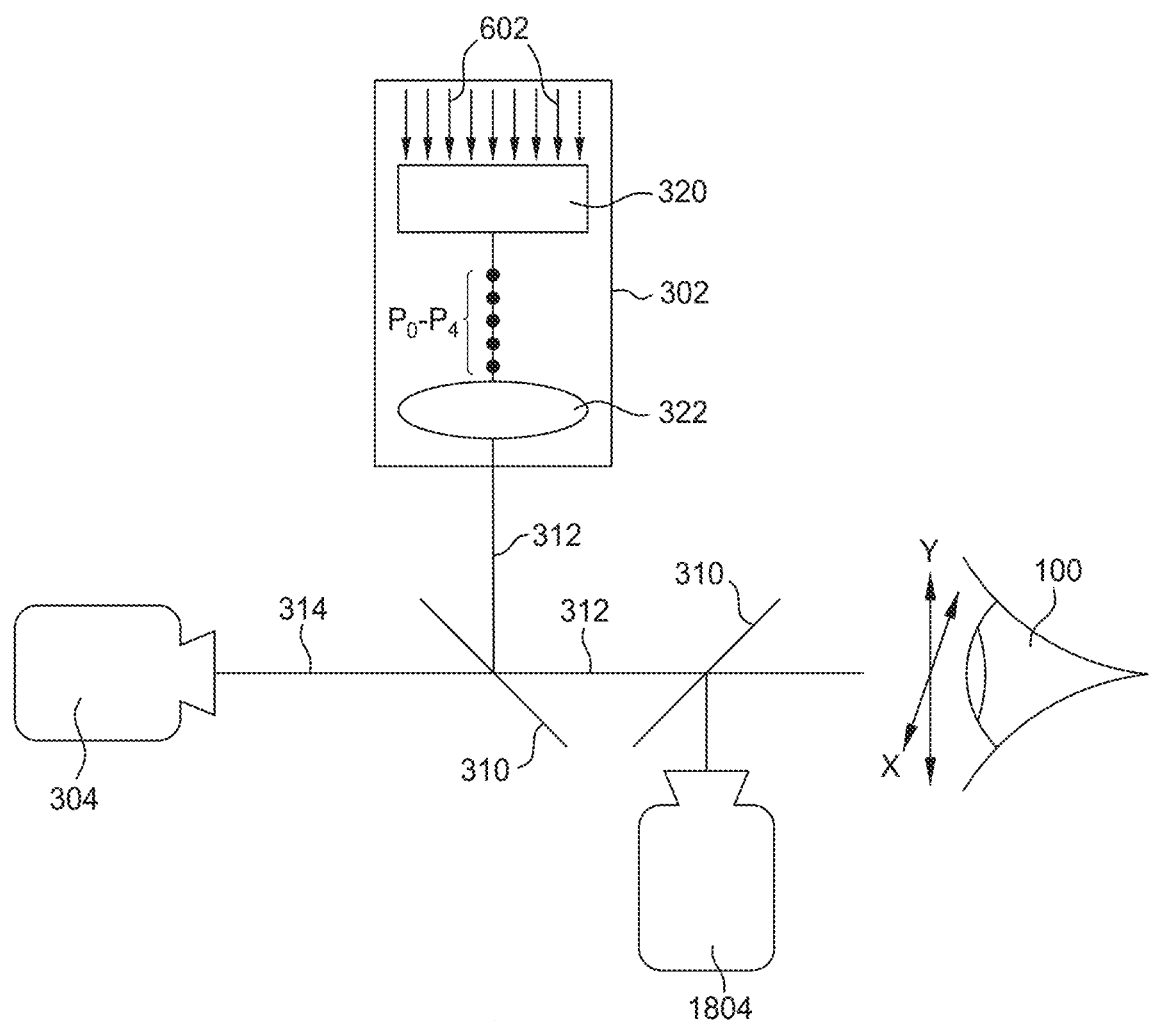
FIG. 18 illustrates a schematic diagram of the visual axis identification system of FIG. 3 including a second camera, according to certain embodiments of the present disclosure.

FIG. 18 illustrates a simplified schematic diagram of an alternative visual axis identification system 1800, according to certain embodiments of the present disclosure. As depicted, the visual axis identification system 1800 is substantially similar to the visual axis identification system 300, but for the inclusion of an additional camera 1804, which may be operably coupled with the processing system 306 (shown in FIG. 3) and/or camera 304 to trigger image capture by the camera 304. The camera 1804 is focused on the retina of the eye 100, and therefore, may be a fundus-type camera. In certain embodiments, the camera 1804 monitors or surveys the retina for the formation of images, such as the images $C_0$-$C_4$, on the retina corresponding to the fixation light spots generated by the fixation light source 302. Upon overlap of the images $C_0$-$C_4$ on the retina, the camera 1804 may recognize the overlap event and trigger the camera 304 (e.g., by either directly communicating with camera 304 or through processing system 306) to record or capture images of the iris plane of the eye 100. As described above, when the images $C_0$-$C_4$ overlap on the retina, the visual axis 110 aligns with the optical axis 312 which also coincides with the optical center of the camera 304. Therefore, image capture by the camera 304, when the optical center thereof is aligned with the visual axis 110, may be automatically triggered by the camera 1804, thereby eliminating or reducing inaccuracies caused by the patient's limited cooperation skills.

Figure 19:
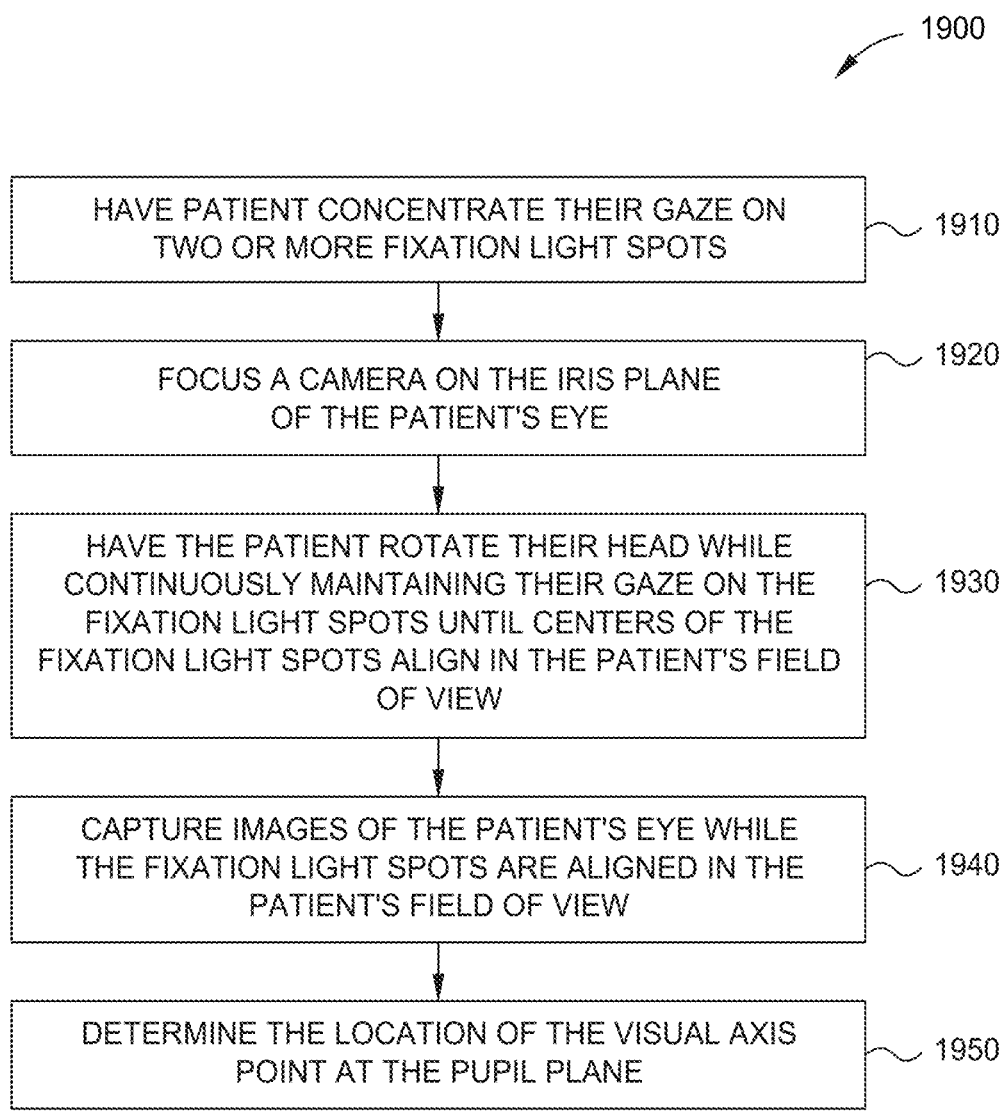
FIG. 19 illustrates a block diagram of a method for using the visual axis identification systems of FIGS. 3, 14A-14B, and 18, according to certain embodiments of the present disclosure.

FIG. 19 illustrates a flow diagram of a method 1900 for determining the location of the visual axis point 112 with the visual axis identification systems 300 and 1800, according to certain embodiments of the present disclosure. Generally, while using the visual axis identification system 300 or 1800, the patient concentrates their gaze on fixation light spots generated by fixation light source 302 at operation 1910. The fixation light spots are focused onto optical axis 312 of the fixation light source 302 and relayed toward the patient's eye 100. At operation 1920, camera 304, having an optical axis 314 aligned with optical axis 312 of the fixation light source 302, is focused on the iris plane of the patient's eye 100. In certain embodiments, the optical center and corresponding optical axis 314 of the camera 304 are marked in the visual field of the camera 304.

At operation 1930, the patient is asked to rotate his or her head while continuously maintaining their gaze on the fixation light spots, until centers of the fixation spots are aligned in the patient's field of view. The patient may move or rotate their head in the X or Y rotational direction to align the centers of the fixation light spots within their field of view. Simultaneously with the movement of the patient's head, the camera 304 captures images or video of the eye 100 while tracking the X/Y position thereof relative to the X/Y position of the optical axis 314. In certain embodiments, tracking of the relative X/Y position of the eye 100 is carried out using the signatures of the blood vessels of the sclera, such as the scleral veins described above. In certain embodiments, the patient is asked to rotate his or head to align the fixation spots during a "test" or "trial" period wherein the camera 304 does not capture images of the eye 100. For example, the patient may be asked to practice such movement during a trial period of about 30 seconds, after which a "measurement" period is commenced and the camera 304 begins capturing images or video.

In certain embodiments, the centers of the fixation spots are aligned at operation 1940 and the patient is asked to maintain the aligned nature or state of the fixation light spots while the camera 304 continues to capture images or video of the patient's eye 100. For example, the patient maintains the aligned state of the fixation light spots for a desired period of time, such as about 30 seconds, while the camera 304 continuously or intermittently records the X/Y position of the eye 100 and relays the images to the processing system 306. The processing system 306 may then analyze the video or series of images at operation 1950 to determine the average X/Y location of the optical axis 314 of the camera 304 in relation to the X/Y location of the eye 100, thus compensating for any unintended eye and/or head movement of the patient. Accordingly, the identification of the average X/Y location of the optical axis 314 corresponds with an approximated X/Y location of the visual axis point 112.

In certain other embodiments, the second camera 1804 monitors the retina of the patient's eye 100 at operation 1940 and automatically triggers the camera 304 to capture images of the eye 100 upon alignment of the corresponding images of the fixation light spots on the retina. The utilization of the second camera 1804 enables automatic image capture of the eye 100 upon alignment of the optical axis 314 with the visual axis 110, thereby eliminating or greatly reducing any inaccuracies caused by unintended eye and/or head movement of the patient, as well as patients having limited collaboration skills. After image capture by the camera 304, the images are analyzed by the processing system 306 at operation 1950 to determine the X/Y location of the visual axis point 112.

The methods and apparatus described above provide a novel visual axis identification system that may be utilized to improve the efficacy of ophthalmic procedures, such as presbyopic treatments including the fitting of corrective lenses, refractive surgery, artificial lens implants, and multifocal corneal inlays. The described visual axis identification systems may further be utilized in combination with any suitable ophthalmic diagnostic devices. Examples of suitable diagnostic devices include corneal topographers, optical coherence tomographers, wavefront meters (e.g., aberrometers), image-guided biometers, surgical microscopes, and other image-based diagnostic devices. In some examples, the visual axis identification systems 300 and 1800 may be utilized in combination with the Verion™, Topolyzer®, ORA™ System, LenSx®, LuxOR™ LX3 platforms manufactured by Alcon, Fort Worth, Texas. In some examples, the visual axis identification systems 300 and 1800 may be utilized with ophthalmic platforms provided by other manufactures.

While the foregoing is directed to embodiments of the present disclosure, other and further embodiments of the disclosure may be devised without departing from the basic scope thereof, and the scope thereof is determined by the claims that follow.

What is claimed is:

1. A method for determining a location of a visual axis point of a patient's eye, comprising:
   directing, with a fixation light source, a fixation light towards the patient's eye, the fixation light comprising two or more fixation light spots formed at different positions along an optical axis of a fixation light source and corresponding with two or more images formed on or near a retina of the patient's eye;
   monitoring, by a retina monitoring camera focused on the retina of the patient's eye, and generating an indication upon recognizing when the centers of the two or more images are coinciding;
   receiving, in an image capture camera, the indication that the centers of the images are coinciding from the retina monitoring camera, thereby automatically triggering the image capture camera to capture one or more digital images of an iris plane of the patient's eye upon centers of the two or more images formed on or near the retina coinciding in a view of the patient while an optical center of the image capture camera is aligned with the optical axis upon which the fixation light spots are formed; and
   identifying the location of the visual axis point at the iris plane based on the one or more digital images, the location of the visual axis point corresponding with an X/Y location of the optical center of the first camera relative to an X/Y location of the patient's eye as displayed in the one or more digital images.

2. The method of claim 1, wherein the location of the visual axis point further corresponds with an X/Y location of the optical axis of the fixation light source at the iris plane when the centers of the images coincide in the patient's view.

3. The method of claim 1, wherein:
   the one or more digital images comprise a plurality of images; and
   identifying the location of the visual axis point of the patient's eye further comprises spatially averaging X/Y locations of the optical center of the first camera relative to X/Y locations of the patient's eye as displayed in a corresponding plurality of digital images.

4. The method of claim 3, wherein the plurality of images are captured over a time period of about 30 seconds.

5. The method of claim 1, further comprising:
   determining the X/Y location of the patient's eye by mapping and tracking vasculature within a sclera of the patient's eye.

6. The method of claim 1, wherein the capturing the one or more digital images is triggered by a user upon receiving an indication from the patient that the centers of the images are coinciding and receiving, in an image capture camera, the indication that the centers of the images are coinciding from the retina monitoring camera.

7. A system for determining a location of a visual axis point of a patient's eye, comprising:
  a fixation light source configured to generate two or more fixation light spots at different positions along an optical axis;
  a retina monitoring camera focused on the retina of the patient's eye, wherein the retina monitoring camera monitors the retina and generates an indication upon recognizing when the centers of the two or more images are coinciding;
  an image capture camera configured to capture digital images of a iris plane of the patient's eye and track an X/Y location of the patient's eye while an optical center of the first camera is aligned with the optical axis upon which the fixation light spots are generated and to receive the indication that the centers of the images are coinciding from the retina monitoring camera, thereby automatically triggering the image capture camera to capture one or more digital images of an iris plane of the patient's eye; and
  a processing system configured to identify the location of the visual axis point at the iris plane based on the one or more digital images captured by the first camera, wherein the visual axis point of the eye corresponds to an X/Y location of the optical center of the first camera relative to the X/Y location of the patient's eye when centers of images formed by the two or more fixation light spots on or near a retina of the patient's eye coincide in a view of the patient.

8. The system of claim 7, wherein the processing system being configured to identify the location of the visual axis point of the patient's eye comprises the processing system being configured to:
  average X/Y locations of the optical center of the first camera in relation to X/Y locations of the patient's eye during a time period in which the patient maintains their gaze on the fixation light source such that the patient observes coinciding centers of the images.

9. The system of claim 7, wherein the first camera is configured to map and track vasculature within a sclera of the patient's eye to determine the X/Y location of the patient's eye.

10. The system of claim 7, wherein the first camera is an infrared camera.

11. The system of claim 7, wherein the fixation light source further comprises a multiplexer configured to generate the two or more fixation light spots from incoming light, and wherein the multiplexer is one of a bifocal lens, multifocal diffractive lens, coated lens, Fabry-Perot-type system, nondiffractive Bessel beam generator, or interferometer.

* * * * *